United States Patent
Aulbach et al.

(10) Patent No.: US 8,214,020 B2
(45) Date of Patent: Jul. 3, 2012

(54) METHOD AND SYSTEM FOR CORRELATING TOMOGRAPHICALLY CONTROLLED INTERVENTIONAL PROCEDURES WITH PATIENT POSITION IN THE RESPIRATORY CYCLE

(75) Inventors: Peter Aulbach, Forchheim-Kersbach (DE); Gabriel Haras, Mücke (DE)

(73) Assignee: Siemens Aktiengesellschaft, Munich (DE)

( * ) Notice: Subject to any disclaimer, the term of this patent is extended or adjusted under 35 U.S.C. 154(b) by 999 days.

(21) Appl. No.: 12/101,268

(22) Filed: Apr. 11, 2008

(65) Prior Publication Data

US 2009/0112083 A1 Apr. 30, 2009

(30) Foreign Application Priority Data

Apr. 12, 2007 (DE) .......................... 10 2007 017 269

(51) Int. Cl.
*A61B 5/00* (2006.01)
(52) U.S. Cl. ...................................... 600/425; 600/427
(58) Field of Classification Search .................. 600/413, 600/428, 427, 425
See application file for complete search history.

(56) References Cited

U.S. PATENT DOCUMENTS 6,076,005 A * 6/2000 Sontag et al. ................. 600/413
7,769,430 B2 * 8/2010 Mostafavi ..................... 600/428

FOREIGN PATENT DOCUMENTS

WO WO 03/084405 10/2003

OTHER PUBLICATIONS

"Intermittent-Mode CT Fluoroscopy-Guided Biopsy of the Lung or Upper Abdomen With Breath-Hold Monitoring and Feedback: System Development and Feasibility," Carlson et al, Radiology, vol. 229, No. 3 ( 2003) pp. 906-912.

* cited by examiner

Primary Examiner — Jacqueline Cheng
(74) Attorney, Agent, or Firm — Schiff Hardin LLP (57) ABSTRACT

In a method and an imaging system for implementing a CT-assisted or MRT-assisted minimally-invasive interventional procedure at an anatomical location inside the body of a patient, the inspiratory or respiratory position of the patient within the respiratory cycle of the patient is continuously detected and a measurement value, identifying a current position of the patient within the respiratory cycle, is detected at a point in time that a CT or MRT slice image of the anatomical location is obtained. This measurement value is stored together with the image data of the slice image so that the measurement value and the image data can be retrieved together and displayed together.

11 Claims, 4 Drawing Sheets

FIG. 5

METHOD AND SYSTEM FOR CORRELATING TOMOGRAPHICALLY CONTROLLED INTERVENTIONAL PROCEDURES WITH PATIENT POSITION IN THE RESPIRATORY CYCLE

BACKGROUND OF THE INVENTION

1. Field of the Invention

The present invention concerns an image acquisition system usable in the field of diagnostic and interventional radiology as well as a method for implementation of CT-controlled or MRT-controlled minimally-invasive interventional procedures for internal organs, tissue regions, lesions (for example in the region of lungs and liver) or pathological structures inside the body of a patient (for example at tumor sources, metastases, hematomas, abscesses etc.) in correlation with the patient's inspiratory or expiratory position (phase) within the respiratory cycle, which serves to improve the precision and safety of the minimally-invasive procedures, in particular in the field of diagnosis tissue sample extraction (biopsy) implemented under CT-assisted or MRT-assisted imaging monitoring after local anesthesia as well as in tumor and pain therapy.

2. Description of the Prior Art

Today the histomorphological and cytomorphological examination of tissue samples is an indispensable method for clinical assessment of a number of benign and malignant clinical situations. Today histological (tissue structure) examination can be applied to all organs due to perfected extraction and examination methods. Hematological diagnostics from bone marrow, spleen and lymph nodes as well as tumor diagnostics from mammary glands, lungs, liver, thyroid and prostate are of particular importance. Cerebrospinal fluid (liquor cerebrospinalis) and effusions from the pleural cavity (cavitas pleuralis) or the abdominal cavity have been able to be obtained by centesis and cyto-diagnostically examined for a long time. An important addition to this is centesis (puncture) cytology that is used for the grading of malignant tumors, cancer precautions and early cancer detection. Today there is thus practically no specific therapy without preceding histological or cytological confirmation of the diagnosis.

The rapid development of imaging methods, in particular sonography, as well as computed tomography in the 1970s, allowed an improved localization of pathological findings since an exact and overlap-free representation of soft tissue structures could be achieved. During the same time period, great advances were made in the precision of the interpretation of tissue fragments. For histological clarity or in the case of an unclear finding, centesis implemented under computer-tomographical or sonographical monitoring represents a suitable technique for clarification. Today percutaneous punch biopsy and needle puncture procedures have developed into an important instrument in diagnostics and therapy monitoring.

Today locally occurring tumors or metastases (for example in the region of the liver or lung) can be safely diagnosed through a percutaneous, minimally-invasive procedure by means of fine needle biopsy and can be treated without implementation of surgery. For this purpose, special probes or hollow needles (puncture needles) are inserted through the skin into the tumor to be treated. Depending on the method, the tumor can then be therapeutically treated locally by action of cold or heat, or chemically. The selection of the respective interventional method is made on the basis of the size, position and condition of the tumor in question. The destroyed tumor is broken down by the body after the procedure and the treated tissue scars over. In order to be able to implement the placement of the probe or needles as precisely as possible, the procedures (for example radio-frequency ablation, cryotherapy or alcohol ablation) are typically implemented under slice image monitoring. Both magnetic resonance tomography and computed tomography are used for this purpose. All of these methods are normally conducted under local anesthesia and allow an implementation of the respective procedure with millimeter precision. Depending on the size and position of the tumors it may be necessary to use a number of probes simultaneously and to repeat the procedures.

In cryotherapy the tissue destruction ensues by a rapid cooling of the tumor tissue to temperatures between −50° C. and −150° C. with the use of a coolant (for example argon gas) inserted into a probe. This leads to an irreversible destruction of the cells as well as a sealing of the smallest arteries and veins. A characteristic of the cryo-treatment is the almost complete absence of pain since the cold inherently has an analgesic effect, and an additional pain therapy (local anesthesia) is not required. The extent of the frozen tumor can be depicted very well by magnetic resonance tomography. A high precision of the tissue destruction during the treatment is thus possible.

Radio-frequency therapy (RF ablation) is a hyperthermic ablation method for cancer therapy that destroys a primary tumor or a metastasis via heat. The heat is achieved by a flexible probe that is inserted into the tumor source under ultrasound or CT monitoring. A radio-frequency alternating current that leads (via the probe) to a temperature increase in the tissue to 90° C. to 120° C. is generated via a radio-frequency generator. The tumor is thereby necrotized in situ. The advantage of the RF ablation lies in the small diameter of the probes used (approximately 2 mm) and the achievable lesion size (up to 5 cm without probe displacement). The monitoring of the tumor destruction ensues depending on the employed apparatus, for example via a direct or indirect temperature measurement or a determination of the conductivity of the tissue or its impedance during the procedure. This occurs through the probe itself; additional probes are not required. After a successful tumor treatment the puncture path is coagulated during the probe removal, i.e. is sealed by the effect of heat. Spreading of the tumor cells thus does not occur. Since the heat treatment of metastases or tumors can be painful depending on the position and organ, the procedure occurs under liberal administration of analgesics or anesthesia. The duration of the procedure is approximately one hour depending on the size and number of the treated metastases.

In alcohol ablation, a tumor to be treated is obliterated with the use of high concentration of alcohol solution. The tumor is thereby punctured with one or more fine puncture needles under CT or MRT monitoring with local anesthesia. Given correct needle position the injection occurs with 95% alcohol mixed with some anesthesia agent in the center of the tumor. Depending on the tissue condition, tumor type and localization, the quantity of alcohol varies between 5 ml and 50 ml. A repeated treatment can be required in the case of larger tumors. The effect of the alcohol is based on a dehydration of the cells, denaturing of protein and thrombosis of the smallest vessels. The consequence is a coagulation necrosis that is subsequently broken down by the body and scarred over. This technique has proved to be particularly effective for treating hepatocellular carcinoma (HCC) since this type of carcinoma exhibits a tumor cyst and the alcohol homogeneously distributes within the tumor. The distribution of the alcohol can be unpredictable in the case of liver metastases, so in these cases the success of this treatment is not exactly predictable. The minimal controllability of the alcohol distribution for liver metastases (with the exception of HCC) as well as the pain stress given positions of the tumors near the cyst are disadvantages. The indication for alcohol ablation thus very much depends on the condition, consistency and localization of the tumor in question.

Transarterial chemo-embolization (TACE) is a conservative but effective therapy method for treatment of hepatocellular carcinoma. An obliteration of the tumor tissue by targeted administration of a chemotherapy compound (epirubicin) by a precise injection is enabled through an access from the groin with a flexible, thin catheter. A very high concentration of the medicine is achieved in the tumor via this method while the exposure of the rest of the body regions due to the chemotherapy is relatively slight.

CT-controlled puncture of tissue or organs with subsequent cytological and histological (fine-tissue) examination of the puncture specimen, CT-controlled drainage treatment as well as CT-controlled neurolysis and facet block count are among the further applications of computed tomography in the field of diagnostics and minimally-invasive therapy.

CT-controlled diagnostic puncture is a conservative method in which, after disinfection of the skin and local anesthesia, a hollow needle is inserted under CT-based fluoroscopy monitoring into a tissue region or an organ of a patient to be examined, whereupon tissue samples (biopsies) are extracted, for example in order to be able to reliably classify the nature of a localized tumor as benign or malignant. A local anesthesia is normally sufficient. The extracted tissue samples are subsequently sent to a medical laboratory for histological exam. This diagnosis method is in particular applies when unclear expansive lesions are to be differentiated in the region of the thorax and the abdomen (for example in the lungs, kidneys, lymph nodes or liver).

A CT-controlled drainage is a minimally-invasive method in which detected abscesses (pus accumulations) and infected hematomas inside the body of a patient are drained out through an interventional procedure via a percutaneously inserted drainage catheter under CT-controlled imaging monitoring. After a suspicion diagnosis posed using CT slice exposures, a CT-controlled puncture is initially implemented to ensure the diagnosis and the microbiological germ and resistance determination. The percutaneous drainage then ensues via the same penetration point. The procedure is analogous to the CT-controlled tissue sample extraction, with the difference that now a drainage tube remains that allows a drainage and irrigation of the pathological fluid accumulation.

In a CT-controlled neurolysis and facet block, specific nerve bundles are switched off via targeted injection of suitable substances (alcohol and anesthesia) under CT monitoring for the purpose of pain therapy (for example in the case of certain spinal column illnesses) or to improve the peripheral arterial blood circulation. The interventional procedure is advantageously implemented in the prone position. If a prone position is not possible with a particular patient, a position must be selected that can be maintained for the entire duration of the procedure and that simultaneously allows the physician an easy access to the point of the body to be treated. As is the case before any procedure, possible risks of the treatment and the measurement of his blood values are explained to the patient. In a facet block procedure, pain treatment of the small zygoapophyseal joints (facets) in the spinal column ensues by injection of a locally effective anesthetic and triamcinolone (a relatively long-acting cortisone preparation) into the facet joints.

In a periradicular therapy (PRT), which (in the case of a herniated intervertebral disc) is in particular indicated as a pain therapy method for treatment of the nerve root exiting from the spinal canal of the spinal column between the lumbar vertebrae, a fine puncture needle is fed into the immediate proximity of the existing spinal cord nerves under local anesthesia and computer tomography imaging. There medicine containing a corticosteroid is then injected which should cause a decrease of the local tissue swelling and thus a "release" of clamped nerves.

In principle there are two possibilities for CT-assisted visual monitoring of a minimally-invasive intervention. The treating physician can generate an individual CT slice exposure (for example via actuation of a foot switch) without table feed in order to acquire a current projection representation of an organ or tissue region to be treated as well as image information with regard to the position of an inserted puncture needle, a probe or another medical instrument typically used for implementation of an interventional procedure. After generation of the exposure, it can occur that the considered CT slice plane shifts as a result of a body movement of the patient or due to inhalation or exhalation. The radiologist implementing the interventional procedure then has the possibility to monitor the position of the needle tip with the use of the aforementioned CT slice exposure in order to be able to alter the needle position without real-time image monitoring. The physician thus does not see the penetration and advancement of the puncture needle on a screen terminal in real time, but only when the physician generates the next CT slice exposure by re-actuation of a foot switch. In contrast to this, the second possibility is to generate images in a continuous sequence in CT fluoroscopy. The possibility of a real-time monitoring of therapeutic or diagnostic procedures thereby exists. Medical instruments inserted into a penetration point can thereby be continuously tracked on the monitor. The radiation exposure of both the radiologist and the patient, however, is problematically distinctly increased relative to the previously illustrated individual image acquisition.

SUMMARY OF THE INVENTION

Starting from the aforementioned prior art, an object of the present invention is to increase the precision and safety of CT-controlled or MRT-controlled, minimally-invasive interventional procedures.

This object is achieved in accordance with the present invention by a method usable (in particular in the field of diagnostic and interventional radiology) for implementation of a CT-controlled or MRT-controlled, minimally-invasive intervention at internal organs, tissue regions, lesions (for example in the area of spinal cord nerve roots) or pathological structures inside the body of a patient (for example at tumor sources, metastases, hematomas, abscesses etc.). In the inventive method, the position within the respiratory cycle in an inspiration and/or expiration state of the patient is continuously detected; and a respective measurement value detected at the point in time of the acquisition of a CT or MRT slice image of the organ, tissue regions, lesions or pathological structures to be treated. The measurement value reflects the current position of the patient within the respiratory cycle, and is stored together with the image data of this CT or MRT slice image such that they can be retrieved, and the measurement value is displayed. In addition to the acquired CT or MRT slice image, which enables a direct comparison of the current anatomical state of this patient with the acquired state, a radiologist implementing the interventional procedure has at hand a further decision criterion in order to assess or monitor whether the tip of a puncture needle used to implement the minimally-invasive procedure is at the correct point that was suitably established before implementation of the procedure.

This is always the case only when the currently detected and indicated position of the patient within the respiratory cycle coincides with the position within the respiratory cycle stored together with the acquired CT or MRT slice image.

According to the invention, a CT or MRT scan is automatically initiated when the inspiratory or expiratory pulmonary pressure that is developed by the lungs of the patient (and therewith the breathing volume in the inspiration or expiration state of the patient) moves around a predeterminable threshold within a tolerance range bounded by two predeterminable thresholds of different magnitudes after issuing a breath-hold command. According to the invention, the CT or, respectively, MRT scan is automatically ended as soon as the inspiratory or expiratory pulmonary pressure assumes values outside of the tolerance range bounded by the two predeterminable thresholds.

The values of the inspiratory or expiratory pulmonary pressure are continuously detected as long as the lower of the two thresholds is not exceeded or the upper of the two thresholds is exceeded. The associated values of the inspiratory or expiratory breathing volume and/or the points in time of these thresholds being exceeded or not are protocolled in a time-discrete and value-discrete manner in a report file at the end of each CT or MRT scan process.

According to the invention, the signal amplitude of an analog measurement signal proportional to the detected inspiratory or expiratory pulmonary pressure can be indicated by an optical, acoustic and/or haptic signal upon an under-run of the lower of the two thresholds or upon an over-run of the upper of the two thresholds. According to the invention, the signal amplitude of the analog measurement signal proportional to the detected inspiratory or expiratory pulmonary pressure is indicated, for example, by illumination of a corresponding number of light-emitting diodes of at least one light-emitting diode row to the left and right of a light-emitting diode emitting light of a different color upon under-run of the lower of the two thresholds or upon over-run of the upper of the two thresholds. The light-emitting diode that emits light of a different color is mounted in the middle of this at least one light-emitting diode row.

According to the invention, after conclusion of a CT or MRT scan the two preset thresholds can be respectively, automatically adapted to the minimal value (detected during this scan process and protocolled in the aforementioned report file), or to the maximal value (likewise detected during this scan and protocolled in the report file) of the detected inspiratory or expiratory pulmonary pressure, insofar as this minimal value or this maximal value lies within the tolerance range bounded by the two thresholds.

Alternatively, after conclusion of a CT or MRT scan, the two preset thresholds can respectively, automatically be adapted to the minimal value (determined over all preceding CT or MRT scan processes and protocolled in the aforementioned report file), or to the maximal value (likewise determined over all preceding CT or MRT scan processes and protocolled in the aforementioned report file) of the detected inspiratory or expiratory pulmonary pressure, insofar as this minimal value or, respectively, this maximal value lies within the tolerance range bounded by the two thresholds.

According to the invention, at the end of each CT or MRT scan, a calibration signal can be generated with which the predeterminable desired value of the measured inspiratory or expiratory pulmonary pressure is automatically established at an intermediate value between the minimal value (detected during this CT or MRT scan and protocolled in the report file) and the maximal value (likewise detected during this scan process and protocolled in the report file) of the inspiratory or expiratory pulmonary pressure. The intermediate value is thereby selected such that it lies within the tolerance range bounded by the two thresholds.

Alternatively, at the end of each CT or MRT scan process a calibration signal can be generated with which the predetermined desired value of the measured inspiratory or expiratory pulmonary pressure is automatically established at an intermediate value between the minimal value (determined over all preceding CT or MRT scan processes and protocolled in the aforementioned report file) and the maximal value (likewise determined over all preceding CT or, respectively, MRT scan processes and protocolled in the aforementioned report file) of the inspiratory or expiratory pulmonary pressure. The intermediate value is thereby selected such that it lies within the tolerance range bounded by the two thresholds.

The object also is achieved in accordance with the present invention by an image acquisition system for generation of image data that are required for CT-assisted or MRT-assisted imaging monitoring of a minimally-invasive intervention at internal organs, tissue regions, lesions (for example in the region of the spinal cord nerve roots) or pathological structures inside the body of a patient (for example at tumor sources, metastases, hematomas, abscesses etc.). The image acquisition system has a control device that causes a measurement value, reflecting the current position within the respiratory cycle (the inspiratory or expiratory state of the patient) at the point in time of the acquisition of a CT or MRT slice image of the organs, tissue regions, lesions or pathological structures to be treated, to be stored together with the image data of this CT or MRT slice image such that it can be retrieved and displayed with the image.

According to the invention the control device can be programmed to automatically initiate a CT or MRT scan process when the inspiratory or expiratory pulmonary pressure of the patient moves around a predeterminable desired value within a tolerance range bounded by two predetermined thresholds of different values after a breath-hold instruction to the patient, and to automatically end the CT or MRT scan when the inspiratory or expiratory pulmonary pressure of the patient assumes values outside the tolerance range bounded by these two predeterminable thresholds.

The inventive image acquisition system moreover has a threshold evaluator formed as a window discriminator and connected with a measurement signal input of the control device, the threshold evaluator supplies a binary output signal that (assuming positive logic) only assumes the value of "logical one" when the detected inspiratory or expiratory pulmonary pressure of the patient moves within a tolerance range bounded by the two predeterminable thresholds.

Using a pneumograph that serves for continuous measurement of the inspiratory or expiratory pulmonary pressure, changes in the length of an expandable respiratory belt (wrapped around the upper abdomen or around the lower chest region of the patient) occurring in the inspiration and expiration process are detected and translated by a pressure-sensitive, piezoresistive, capacitive or inductive transducer into an analog measurement signal that is directly proportional to the detected inspiratory or expiratory pulmonary pressure.

Furthermore, the inventive image acquisition system has a respiration monitoring and display system with at least one display unit which is used to display the signal amplitude of a measurement signal proportional to the detected inspiratory or expiratory pulmonary pressure of the patient via a light signal of the at least one display unit.

According to the invention, the two thresholds and/or the desired value can be predetermined by a calibration and control unit integrated into the inventive image acquisition system.

The inventive image acquisition system moreover has a radio wave transmission and reception system with a radio wave transmitter for wireless transmission of two of the pulmonary pressure thresholds predetermined by the calibration and control unit to a radio wave receiver connected with a programmer signal input of the window discriminator and/or for wireless transmission of a desired pulmonary pressure value predetermined by the calibration and control unit to a radio wave receiver connected at the output with the display units of the respiration monitoring and display system.

Moreover, a further radio wave transmitter can be provided which serves to transfer the measurement signal delivered by the pressure-sensitive piezoresistive, capacitive or inductive transducer of the pneumograph and proportional to the detected inspiratory or expiratory pulmonary pressure of the patient wirelessly to a radio wave receiver of the radio wave transmission and reception system that is connected with the display units of the respiration monitoring and display system and/or to a radio wave receiver of this radio wave transmission and reception system that is connected with the programmer signal input of the window discriminator.

The above object also is achieved in accordance with the present invention by a computer software program product (computer readable medium encoded with programming instructions) that causes the method described above to be implemented by a control unit with an associated screen terminal of an image acquisition system described above.

DESCRIPTION OF THE PREFERRED EMBODIMENTS

In the following paragraphs the system components of the inventive image acquisition system and the steps of the associated inventive method are described in detail using the attached drawings, starting from a system and method known from the prior art for CT-assisted imaging monitoring of minimally-invasive interventions.

Various image acquisition methods and systems that are used for visualization of internal organs, tissue regions, lesions or pathological structures of a patient that are to be punctured are known from the prior art. One of these systems is described in the medical professional article "Intermittent-Mode CT Fluoroscopy-guided Biopsy of the Lung or Upper Abdomen with Breath-hold Monitoring and Feedback: System Development and Feasibility", (Radiological Society of North America, RSNA, Oak Brook/Ill., December 2003, Vol. 229, Nr. 3, p. 906-912) by Dr. Stephanie K. Carlson et al. This is a CT-based image acquisition system with integrated respiration monitoring and display system MDS (called a "Respiratory Bellows System") which was developed in the Department for Radiology of the Mayo Clinic in Rochester (Minn.) and is used for monitoring and optical feedback of the constancy of the inspiratory or, respectively, expiratory pulmonary pressure (and therefore the breath volume) given a breath-hold of a patient to be examined by means of CT fluoroscopy. Among other things, this system has a pneumograph PG which includes a respiratory belt AG expandable in the form of an air-filled rubber bellows, which respiratory belt AG is wrapped around the upper abdomen or, respectively, around the lower chest region of the patient. The respiratory belt AG is thereby connected via an air-filled rubber tube with a pressure-sensitive, piezoresistive, capacitive or inductive transducer Td with which length changes of the belt (which correspond to the circumference or, respectively, volume changes of the abdomen in the inspiration or, respectively, expiration process, and thus changes of the pulmonary pressure $p_M$ in the respiratory process) are detected in the form of changes of the air pressure inside the rubber tube GS and are converted into an electrical analog signal, for example into an analog measurement voltage $U_M$ directly proportional to the detected pulmonary pressure $p_M$. The measurement signal can be modulated on a radio-frequency analog carrier signal and, for example, be transmitted wirelessly via a Bluetooth interface (including a radio wave transmitter $RFS_1$ and a radio wave receiver $RFE_1$) to a first display unit $AE_1$. This display unit serves to indicate the signal amplitude of the measurement signal corresponding to the respective respiration state (i.e. the current position within the respiratory cycle) of the patient by illuminating a corresponding number of light-emitting diodes of a light-emitting diode row $LZ_1$ to the left and right of a light-emitting diode $LED_M$ in the center of this light-emitting diode row $LZ_1$, which light-emitting diode $LED_M$ emits light of a different color. The patient is thereby instructed by a radiologist implementing the examination to hold his or her breath and to inhale or exhale only on command. Only the middle light-emitting diode $LED_M$ of the light-emitting diode row $LZ_1$ then illuminates during an inspiratory or, respectively, expiratory breath hold. Since the aforementioned first display unit $AE_1$ is advantageously ergonomically mounted on a support arm TA permanently connected with the patient table PT of a computed tomography scanner CTG and thus can easily be viewed by a patient lying on the patient table PT, the patient has the possibility to monitor the constancy of the breathing himself. The radiologist can continuously track the time curve of the pulmonary pressure on a further light-emitting diode row $LZ_2$ of a second display unit $AE_2$ (likewise connected with the radio wave receive $RFE_1$) which is mounted above a display screen AB serving for graphical visualization of interesting sub-regions of a tissue region or organ to be presented by means of CT-assisted imaging and displays the same signal as the light-emitting diode row $LZ_1$ of the first display unit $AE_1$ that is visible by the patient, and if applicable said radiologist can given further commands to inhale, exhale and/or hold breath dependent on said time curve.

The respiratory monitoring and display system MDS described in the preceding can thereby be controlled with the aid of a calibration and control unit KSE. This calibration and control unit KSE in particular serves to adjust a pressure reference value $p_{M0}$ (desired value) to which the deviations of the inspiratory or expiratory pulmonary pressure (shown by the light-emitting diode rows $LZ_1$ or $LZ_2$ of the two display units $AE_1$ and $AE_2$) should be related immediately before and during a CT scan process. The establishment of this pressure reference value can thereby ensue by momentarily throwing a switch KS at a specific value of the pulmonary pressure $p_M$ or by inputting a specific pressure value via a programmer or, respectively, data input interface (not shown).

The calibration and control unit KSE can be connected to a further radio wave transmitter $RFS_2$ with which an analog voltage signal $U_{M0}$ proportional to a predeterminable desired value $p_{M0}$ of the pulmonary pressure $p_M$ is modulated on a radio-frequency analog carrier signal and is transmitted (for example via Bluetooth) wirelessly to the radio wave receiver $RFE_1$ of the respiratory monitoring and display system MDS described in the preceding. Moreover, the radiologist has the possibility to suitably establish the beginning point in time $t_{SB}$ or the end point in time $t_{SE}$ of a CT scan by the calibration and control unit KSE and to wirelessly transmit a voltage signal $U_{SB}$ (corresponding to the beginning point in time $t_{SB}$) and a voltage signal $U_{SE}$ (corresponding to the end point in time $t_{SE}$) to the central control device ZSE of the image processing system BVS (and via this to the computed tomography scanner CTG) with the use of the radio wave transmitter $RFS_2$.

The RF signals sent from the respiratory monitoring and display system MDS or from the calibration and control unit KSE can in turn be wirelessly received (for example via Bluetooth) by a radio wave receiver $RFE_2$ connected with a measurement data input of the central control device ZSE of the image processing system BVS via an analog-digital converter ADU. Upon receipt by the central control device ZSE of the image processing system BVS of the analog measurement signal $U_M$, a voltage signal $U_{SB}$ establishing the beginning point in time $t_{SB}$ and a voltage signal $U_{SE}$ establishing the end point in time $t_{SE}$, the computer tomography apparatus CTG is instructed to implement a CT scan process of the duration $\Delta t = t_{SE} - t_{SB}$.

Image data provided by the computed tomography apparatus CTG are supplied to the image processing system BVS via an input/output interface I/O. In addition to the central control device ZSE which controls the data exchange with the computer tomography apparatus CTG as well as the data exchange between the individual system components of the image processing system BVS, the image processing system BVS can thereby possess (among other things) suitable pre-processing filters as well as software modules for segmentation and cluster formation (designated as a pre-processing module VVM in the following) as well as an image rendering module BRA for graphical visualization of segmented image regions in a virtual object space in which sub-regions of the tissue region or organ selectable by the radiologist are shown.

Upon receipt of image data from the computed tomography scanner CTG, these can be stored either temporarily or persistently (depending on system configuration) in an external image data storage in preparation for a later graphical visualization. A copy of the image data is supplied via the input/output interface I/O to the pre-processing module VVM (cited in the preceding) which has a digital filter for noise suppression, contrast improvement and edge detection. After filtering the image data are registered by a segmentation and clustering module (likewise contained in the pre-processing module VVM) and (if possible) are merged ("clustered") into groups of similar or like image objects arranged closely next to one another.

At the prompting of the central control device ZSE of the image processing system BVS, the segmented and clustered image data are then read out by an image rendering module BRA (which is required for preparation of the image data for a two- and/or three-dimensional graphical visualization) integrated into the image processing system BVS, rendered and displayed on a display screen AB of a monitor terminal in 2D-rendered and/or 3D-rendered form in correlation with the inspiratory or expiratory position within the respiratory cycle of the patient. For the purpose of optical offsetting from the tissue surrounding them, the individually segmented and clustered image regions can be emphasized via different coloring. In this context both the generation of maximum-intensity projections (MIPs) (method in which voxels of maximum intensity are projected in an image plane, whereby a 3D impression of the imaged tissue structures arises upon consideration from various viewing angles) and a 3D post-processing (volume rendering) by means of thin-slice multiplanar reformations (MPR) (wherein slice images in any arbitrary slice plane are retroactively calculated from a volume data set of a tissue region or organ to be examined that is acquired by means of computer tomography) are possible.

The maximum contrast is achieved by an optimal coordination of the contrast agent bolus injection with the image acquisition as well as via an optimal bolus profile. In addition to what are known as "technical pitfalls" that appear, for example, in the form of sub-volume effects and contrast agent artifacts or, respectively, in the form of a weak contrasting and are caused by an injection speed in the contrast agent bolus injection that is too low, wrong bolus timing, or by a quantity of contrast agent that is too small, respiration and pulsation artifacts (what are called "patient-dependent pitfalls") in particular represent a large problem in this context since these aliasing effects can have a particularly disruptive effect in the framework of the image interpretation. Namely, respiration artifacts can lead to abrupt contrast variations and simulate intraluminal filling defects.

In order to generate optimally few movement artifacts, the image data acquired by means of CT-assisted imaging are therefore typically acquired in the framework of what is known as a continuous expiration CT in the last phase of a forced expiration process. This technique is in particular applied when patients, due to their reduced respiratory reserve, are not in the position to hold their breath sufficiently long enough after expiration in order to depict a tissue region to be examined by means of computer tomography without overlap.

Figure 1:
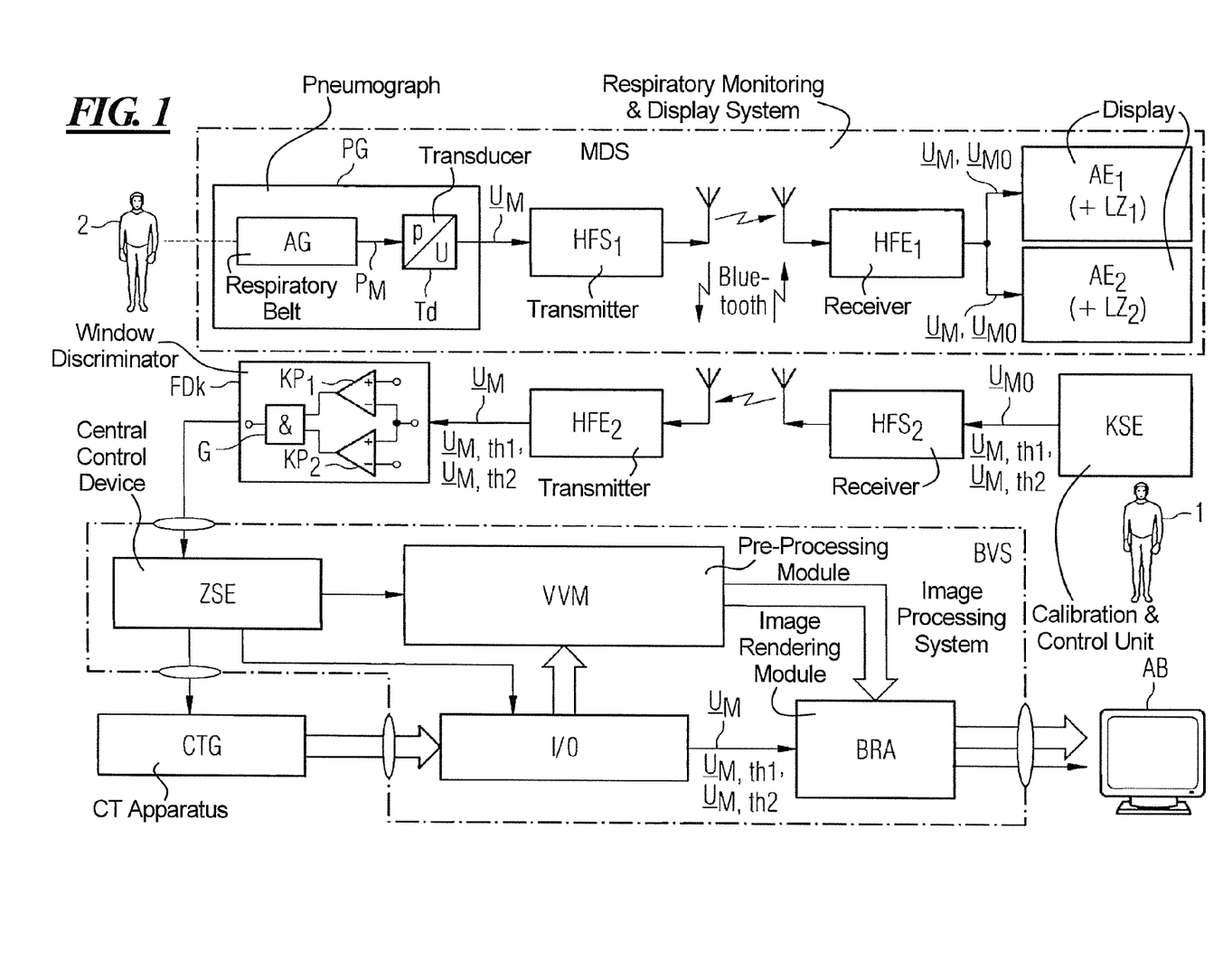
FIG. 1 is a block diagram of an embodiment of an image acquisition system according to the present invention that is used for monitoring and display of the pulmonary pressure as well as for CT-assisted imaging monitoring of a minimally-invasive intervention at internal organs, tissue regions, lesions or pathological structures of a patient that are to be punctured.

A block diagram of an image acquisition system according to an exemplary embodiment of the present invention is shown in FIG. 1, which image acquisition system serves for monitoring and display of the pulmonary pressure as well as for CT-assisted imaging monitoring of a minimally-invasive intervention at internal organs, tissue regions, lesions or pathological structures of a patient to be punctured and is similarly constructed in comparison to the conventional image acquisition system explained in the preceding. The inventive image acquisition system differs from the system illustrated above merely through the use of a threshold decider downstream from the radio wave receiver $RFE_2$ of the image processing system BVS and realized as a window discriminator FDk. This threshold decider delivers a binary output signal that, assuming positive logic, only assumes the value "logical one" when the measurement voltage $U_M$ reflecting the inspiratory or, respectively, expiratory pulmonary pressure $p_M$ moves within a tolerance range bounded by two suitably established thresholds $U_{M,th1}$ and $U_{M,th2}$. The two cited thresholds $U_{M,th1}$ and $U_{M,th2}$ can thereby be predetermined via a calibration and control unit KSE' and be transferred wirelessly via the Bluetooth interface to the radio wave receiver $RFE_2$ of the image processing system BVS.

Via the discriminator circuit FDk (which is composed of two comparator stages $KP_1$ and $KP_2$ connected at the output side with the signal inputs of an AND-gate) it is thus ensured that the aforementioned measurement data input of the central control device ZSE is controlled in a value-discriminated manner. A first comparator stage $KP_1$ of the window discriminator FDk (which first comparator stage $KP_1$ is connected at the output with a first signal input of the AND-gate G) that is charged by an inverted input with the measurement voltage $U_M$ proportional to the detected pulmonary pressure $p_M$ thereby serves for comparison of the amplitude values of this analog signal with the voltage potential of a predeterminable upper threshold voltage $U_{M,th2}$ that is present at a non-inverted input of this first comparator stage $KP_1$. A second comparator stage $KP_2$ of the window discriminator FDk (the second comparator stage $KP_2$ being connected at the output with a second signal input of the AND-gate G) that is charged via a non-inverted input with the measurement voltage $U_M$ proportional to the detected pulmonary pressure $p_M$ serves for comparison of the amplitude values of this analog signal with the voltage potential of a predeterminable lower threshold voltage $U_{M,th1}$ that is present at an inverted input of this second comparator stage $KP_2$.

If the amplitude values of the analog measurement voltage $U_M$ are in a value range below the voltage potential of the upper threshold voltage $U_{M,th2}$, the output voltage $U_{out1}$ of the first comparator stage $\overline{KP_1}$ assumes the voltage potential of its positive saturation voltage $+U_{Sat}$ which (assuming positive logic) corresponds to a "high" level of $U_{out1}$. By contrast, if the amplitude values of the aforementioned measurement voltage $U_M$ use in a value range above the voltage potential of the upper threshold voltage $U_{M,th2}$, the output voltage $U_{out1}$ of the first comparator stage $\overline{KP_1}$ assumes the voltage potential of its negative saturation voltage $-U_{Sat}$ which (assuming positive logic) corresponds to a "low" level of $U_{out1}$.

In the second computer stage $KP_2$ the relationships are difference since the roles of both of the signals present at the non-inverted or, respectively, inverted input of this comparator stage as described in the preceding are swapped relative to those of the first comparator stage $KP_1$. If the amplitude values of the measurement voltage $U_M$ lie within a value range above the voltage of the lower threshold voltage $U_{M,th1}$, the output voltage $U_{out2}$ of the second comparator stage $\overline{KP_2}$ assumes the voltage potential of its positive saturation voltage $+U_{Sat}$ which (assuming positive logic) corresponds to a "high" level of $U_{out2}$. By contrast, if the amplitude values of the aforementioned measurement voltage $U_M$ are in a value range below the voltage potential of the lower threshold voltage $U_{M,th1}$, the output voltage $U_{out2}$ of the first comparator stage $\overline{KP_2}$ assumes the voltage potential of its negative saturation voltage $-U_{Sat}$ which (assuming positive logic) corresponds to a "low" level of $U_{out2}$.

Since a binary signal with "high" level is provided via the output of the aforementioned AND-gate G only when both input signals of this AND-gate (i.e. the two digital output voltages $U_{out1}$ or, respectively, $U_{out2}$ of the comparator stages $KP_1$ and $\overline{KP_2}$) respectively direct "high" levels, a binary signal commanding the initiation of a CT scan process is only relayed to the central control device ZSE of the image processing system BVS when the amplitude values of the analog measurement voltage $U_M$ proportional to the detected pulmonary pressure $p_M$ fall in terms of magnitude into the tolerance range bounded by the two threshold voltages $U_{M,th1}$ and $U_{M,th2}$ of the window discriminator FDk; the inequality chain $\overline{U}_{M,th1} < \overline{U}_M < \overline{U}_{M,th2}$ is thus satisfied. Compliance with this condition is indicated by illumination of a light-emitting diode $LED_M$ emitting green light, which light-emitting diode $LED_M$ is arranged in the middle of the light-emitting diode row $LZ_1$ or $LZ_2$ of the two aforementioned display units $AE_1$ and $AE_2$.

Given non-compliance with the aforementioned condition, the magnitude of deviation between the analog measurement voltage $U_M$ and a voltage level $U_{M0}$ predeterminable by the radiologist and proportional to a suitably established desired value $p_{M0}$ of the measured pulmonary pressure $p_M$ can be indicated (S4') via a light signal emitted by two spatially separated display units $AE_1$ and $AE_2$. The light signal is thereby formed via illumination of a number (corresponding to the respective magnitude of deviation) of light-emitting diodes emitting red light to the left and right of the light-emitting diode $LED_M$ emitting in the green spectral range in the middle of the two light-emitting diode rows $LZ_1$ and $LZ_2$ of these display units $AE_1$ and $AE_2$. The two display units $AE_1$ and $AE_2$ are arranged in an ergonomically advantageous manner so that the display unit $AE_1$ is easily visible by the patient to be examined and the display unit $AE_2$ by the radiologist.

At the end of the CT scan the signal values of $U_M$ are recorded in a report file after translation into the corresponding pulmonary pressure values, which report file is stored in a memory module of a memory unit (not shown). According to the invention, between two CT scans in immediate succession, the two preset thresholds $U_{M,th1}$ and $U_{M,th2}$ can be automatically, respectively reset by the central control device ZSE of the image processing system BVS or by the calibration and control unit KSE' dependent on the stored signal values of $U_M$ in order to adapt the size of the tolerance range to the position of the patient within the respiratory cycle. At the end of a CT scan a calibration signal can optionally also be transmitted from the central control device ZSE of the image processing system BVS or from the calibration and control unit KSE' to the inventive respiratory monitoring and display system MDS', with which calibration signal the desired voltage potential $U_{M0}$ of the measurement voltage $U_M$ proportional to the predeterminable desired value $p_{M0}$ of the pulmonary pressure $p_M$ is automatically reestablished. In this manner it is ensured that the image data acquired in a CT scan process are correlated with the displays of the two display units $AE_1$ and $AE_2$ and consequently with the current position of the patient within the respiratory cycle.

Figure 2:
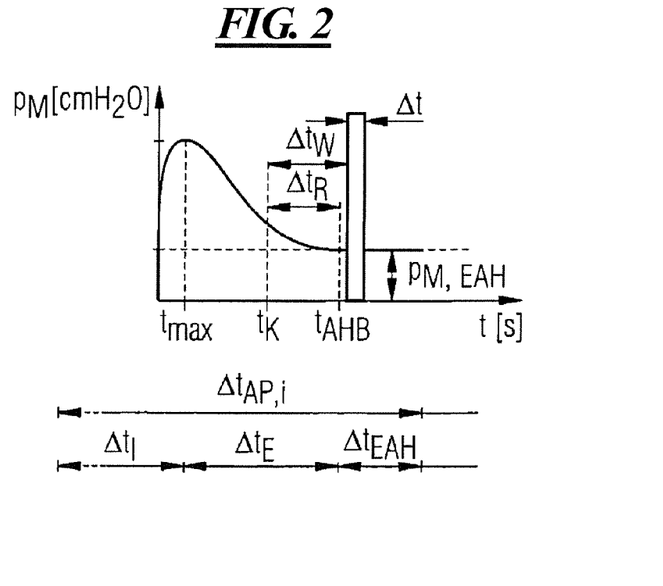
FIG. 2 shows a diagram reproducing the characteristic line curve of the inspiratory or expiratory pulmonary pressure over time during a respiration period of a patient to be examined, with which diagram it is illustrated that a CT scan process for imaging monitoring of a minimally-invasive intervention at internal organs, tissue regions, lesions or pathological structures of the patient is conventionally manually initiated by a radiologist, and in fact at a point in time at which the pulmonary pressure of the patient is at least approximately constant.
Figure 3:
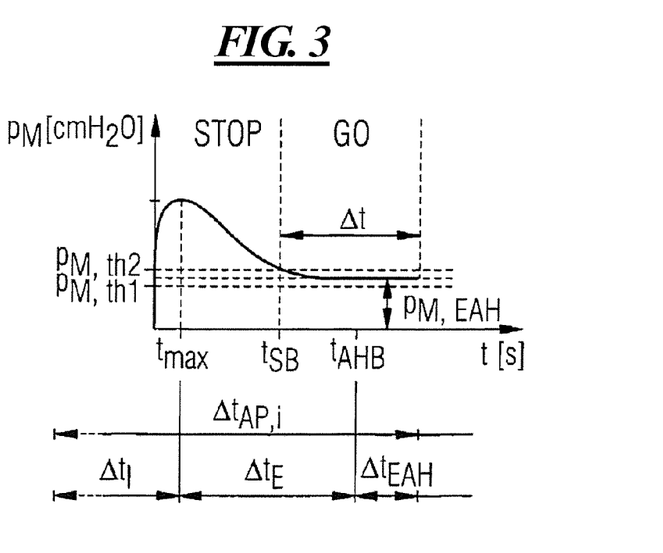
FIG. 3 shows an additional diagram reproducing the characteristic line curve of the inspiratory or expiratory pulmonary pressure over time during a respiration period of a patient to be examined, with which diagram it is illustrated how the beginning point in time and the duration of a CT scan to be implemented are determined according to the present invention.

FIG. 2 shows a diagram reflecting the characteristic line curve of the inspiratory or expiratory pulmonary pressure $p_M$ (in $cmH_2O$) over time t (in s) during a respiration period of duration $\Delta t_{AP,i}$ of a patient, with which diagram it is illustrated how the beginning point in time $t_{SB}$ and the duration $\Delta t$ of a CT scan to be implemented are determined according to the present invention. As is apparent from the diagram, the phase of a CT scan lasts precisely as long as the pulmonary pressure $p_M$ of the appertaining patient moves around a desired value $p_{M0}$ (not shown) within a tolerance range bounded by two predeterminable pressure thresholds $p_{M,th1}$ and $p_{M,th2}$, i.e. as long as the inequality chain $p_{M,th1} < p_{M,EAH} < p_{M,th2}$ is satisfied for a set constant pulmonary pressure value $p_{M,EAH}$ given a breath hold conducted on command. As shown in FIG. 3, given an expiratory breath hold that point in time at which the characteristic breath hold curve falling monotonically in the range of the expiration phase has dropped to the value $p_{M,th2}$ (i.e., to the upper of the two pressure thresholds) consequently arises as a beginning point in time $t_{SB}$ of the CT scan. Conversely, given an inspiratory breath hold that point in time at which the characteristic breath hold curve rising monotonically in the range of the inspiration phase has risen to the value $p_{M,th1}$ (i.e., to the lower of the two pressure thresholds) arises as a beginning point in time $t_{SB}$ of the CT scan. In both cases the end point in time $t_{SE}$ is that point in time at which the patient resumes breathing again; as a result of an inhalation or exhalation, the pulmonary pressure is thus set to a value outside of the tolerance range bounded by the two pressure thresholds $p_{M,th1}$ and $p_{M,th2}$. According to this exemplary embodiment of the present invention, beginning point in time $t_{SB}$ and end point in time $t_{SE}$ of a CT scan to be implemented are thus determined dependent on the acquired characteristic pulmonary pressure curve, meaning that a CT scan is inventively automatically initiated or, respectively, ended dependent on the determined values of $t_{SB}$ and $t_{SE}$.

Figure 4:
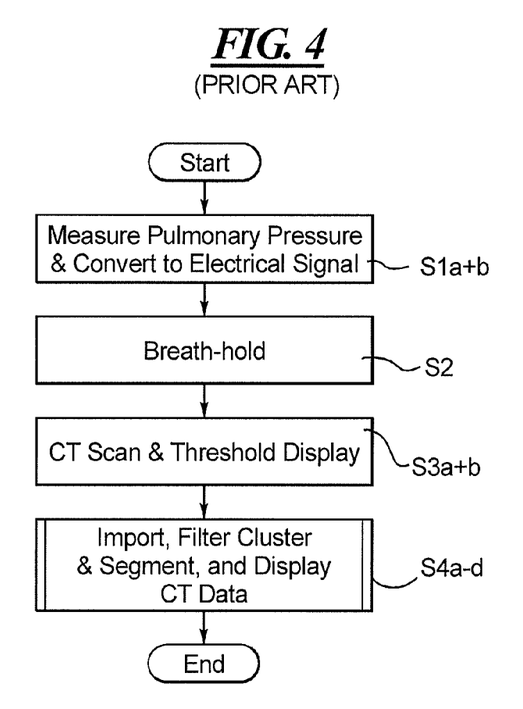
FIG. 4 shows a flowchart representing a conventional method for CT-assisted imaging monitoring of a minimally-invasive procedure implemented at internal organs, tissue regions, lesions or pathological structures of a patient after local anesthesia.

FIG. 4 is a flowchart illustrating a conventional method for CT-assisted imaging monitoring of a minimally-invasive procedure implemented after local anesthesia at punctured internal organs, tissue regions, lesions or pathological structures of a patient. After measurement (S1a) of the pulmonary pressure $p_M$ by detection of circumference or volume changes of the abdomen in an inspiration or expiration event of the patient to be treated and conversion (S1b) of the detected measurement signal into an electrical analog signal (for example into an analog measurement voltage $U_M$), the patient is instructed to hold his breath (S2) through a command of a radiologist conducting the examination. When the measured pulmonary pressure $p_M$ has adjusted to a constant value, the radiologist manually initiates a CT scan (S3a) in order to acquire image data of axial, sagittal and/or coronal cross-section depictions (in the form of greyscale images of a specific resolution) of regions of interest of the internal organs, tissue regions, lesions or pathological structures of this patient that are to be punctured. The magnitude of deviation between the analog measurement voltage $U_M$ and a desired value $U_{M0}$ predetermined by the radiologist is thereby indicated by a light signal (S3b) at two spatially separate display units $AE_1$ and $AE_2$ both before and during the CT scan, which display units $AE_1$ and $AE_2$ are arranged such that the display unit $AE_1$ is easily visible by the patient and the display unit $AE_2$ by the radiologist. The image data acquired by means of computed tomography are subsequently imported into an image processing system BVS (S4a) and an optional pre-processing filtering (S4b) for noise suppression, contrast improvement and edge detection of these image data is implemented. The filtered image data are subsequently subjected to a segmentation and clustering algorithm (S4c) before the characteristic line curve of the measured pulmonary pressure $p_M$ over time t and the image data rendered with the aid of a 2D/3D image rendering application BRA into 2D slice images or 3D reconstructions are visualized on a display screen AB of a monitor terminal in graphical form (S4d).

Figure 5:
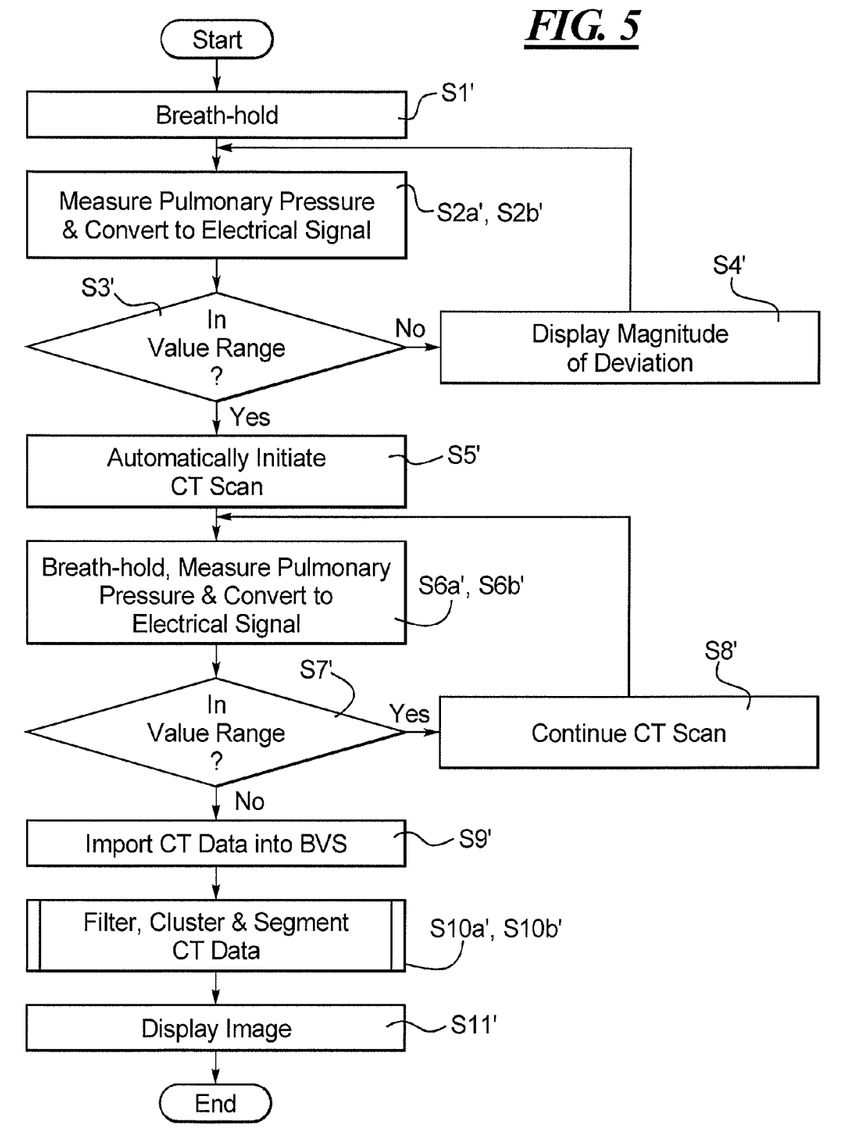
FIG. 5 shows a flowchart representing the inventive method for CT-assisted imaging monitoring of a minimally-invasive procedure implemented after local anesthesia at internal organs, tissue regions, lesions or pathological structures of a patient in correlation with the patient's position within the respiratory cycle.

FIG. 5 is a flowchart of an embodiment of the inventive method for correlating CT-assisted imaging monitoring of minimally-invasive procedures at internal organs, tissue regions, lesions or pathological structures of a patient that are to be punctured, with the inspiratory or expiratory position of the patient within the respiratory cycle. The method, which is implemented using the image acquisition system shown in FIG. 1, begins with the patient being requested by a radiologist conducting the examination to hold his or her breath or to breathe as slowly as possible (S1'). The pulmonary pressure $p_M$ of the patient is thereupon measured in that circumference or volume changes of the abdomen are detected (S2a') in the inspiration or expiration process as well as in the phase of the breath hold and the acquired measurement signal is converted (S2b') by means of a pressure-sensitive transducer Td into an electrical analog signal, for example into an analog measurement voltage $U_M$ proportional to $p_M$. In a step S3' it is queried whether the voltage potential of the measurement voltage $U_M$ relative to ground lies within a value range $]U_{M,th1}, U_{M,th2}[$ predeterminable by the radiologist. If this is not the case, the magnitude of deviation between the analog measurement voltage $U_M$ and a desired value $U_{M0}$ (likewise predeterminable by the radiologist) is indicated (S4') via a light signal on two spatially separate display units $AE_1$ and $AE_2$. The latter are arranged such that the display unit $AE_1$ is easily visible by the patient to be examined and the display unit $AE_2$ by the radiologist. The measurement of the pulmonary pressure $p_M$ is continued during this time, meaning that the method begins anew with step S2a'. Otherwise a CT scan is automatically initiated (S5') by the central control device ZSE of the image processing system BVS in order to acquire image data of axial, sagittal and/or coronal cross-section depictions (in the form of greyscale images of a specific resolution) of regions of interest of the internal organs, tissue regions, lesions or pathological structures of this patient that are to be punctured. The pulmonary pressure $p_M$ is thereby continuously measured via detection of circumference or volume changes of the abdomen in an inspiration or expiration event as well as in the phase of the breath hold (S6a'), and the acquired measurement signal is converted (S6b') into an electrical analog signal, wherein this is in turn an analog measurement voltage $U_M$ proportional to $p_M$. In a step S7' it is then in turn queried whether the voltage potential of the measurement voltage $U_M$ relative to ground is within a value range $]U_{M,th1}, U_{M,th2}[$. If this is the case, the CT-supported imaging process for acquisition of image data of axial, sagittal and/or coronal cross-section depictions is continued (S8') and the method begins anew with step S6a'. If, by contrast, the voltage potential of the measurement voltage $U_m$ lies within the aforementioned value range, the image data acquired by means of computer tomography are imported (S9') into the image processing system BVS. After an optional pre-processing filtering for noise suppression, contrast improvement and edge detection of the acquired image data (S10a'), the filtered image data are subjected to a segmentation and clustering algorithm (S10b'). The method ends with the characteristic line curve of the measured pulmonary pressure $p_M$ over time t and the image data, rendered with a 2D/3D image rendering application BRA into 2D slice images or 3D reconstructions, being presented on a display screen AB of a monitor terminal in graphical form (S11').

Before, during, and after conclusion of the CT scan, the radiologist has the possibility to have the time curve of the inspiratory or, respectively, expiratory pulmonary pressure $p_M$ (detected by the respiratory monitoring and display system MDS and indicated by the in the form of a time-variable light signal emitted by light-emitting diodes of the display unit $AE_2$) displayed in the form of a characteristic pulmonary pressure curve $p_M(t)$ on the display screen AB of the monitor terminal. In this manner the radiologist is placed in the position to assess whether the current position of the patient within the respiratory cycle (i.e. the value of the inspiratory or, respectively, expiratory pulmonary pressure $p_M$ at a monitoring point of time $t_{SE}$ at the end of a CT scan) corresponds to the position within the respiratory cycle during the duration $\Delta t$ of an implemented CT scan or is within a tolerance range around the predetermined desired value $p_{M0}$, which tolerance range is bounded by the thresholds $p_{M,th1}$ and $p_{M,th2}$. If this is the case, work can proceed safely, which is of great importance in a CT-controlled minimally-invasive procedure, for example given the extraction of a tissue sample (biopsy); if this is not the case, corresponding commands to inhale, exhale or hold the breath further can be given to the patient. Moreover, the patient has the possibility to monitor his or her position within the respiratory cycle himself by tracking the display on the display unit $AE_1$ and regulate based on the desired value $p_{M0}$ or, respectively, on a pulmonary pressure value lying within the value range between $p_{M,th1}$ and $p_{M,th2}$. The radiologist can thus be sure that the spatial position and anatomical shape of a sub-region (shown on the display screen AB as a 2D or 2D raster graphic) of the tissue region or organ that is to be examined coincides with the position and shape of this sub-region that is actually dependent on the current position of the patient within the respiratory cycle. Puncture targets (for example in the region of the liver, in the region of the upper abdomen or in the region of the lung) provided for a tissue extraction and dependent on the current position within the respiratory cycle can thus be percutaneously punctured with the aid of a puncture needle. An advantage of the method according to the invention relative to the prior art is thus that puncture errors, which are ascribed to a variation of the respiratory cycle position of a patient to be examined under CT-assisted imaging monitoring that goes unnoticed by the radiologist, can be avoided.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for implementing a tomographically-assisted, minimally-invasive interventional procedure of a patient, comprising the steps of:
   instructing the patient to perform a breath hold and, during said breath hold, measuring a threshold value of a pulmonary pressure in the lungs of the patient;
   continuously detecting successive inspiratory/expiratory positions of the patient by continuously detecting said pulmonary pressure;
   conducting a plurality of tomographic scans of the patient during said interventional procedure and, for each of said scans in said plurality of scans, automatically initiating acquisition of a tomographic slice image of the patient, at an image acquisition time, when the continuously detected pulmonary pressure is within a tolerance range bounded by an upper boundary and a lower boundary of respectively different magnitudes around said threshold value of said pulmonary pressure, said tomographic slice image being comprised of image data;
   automatically ending said image acquisition in each of said scans when said pulmonary pressure assumes a value outside of said tolerance range, each of said scans being defined by the initiating and ending of said image acquisition;
   continuously detecting values of said pulmonary pressure including when said pulmonary pressure is below said lower boundary and when said pulmonary pressure is above said upper boundary, and identifying a plurality of values representing an inspiratory/expiratory breathing volume of the patient from said plurality of values of said pulmonary pressure, and generating a computerized report file of each of said scans that includes a representation of said breathing volume of the patient with respect to time; and
   after each of said scans, identifying an extreme value of said pulmonary pressure, selected from the group consisting of a maximum value and a minimum value, and including the identification of said extreme value in said computerized report file and identifying an average value of the respective extreme values of said plurality of scans and, if said average of said extreme value is within said tolerance range, automatically adapting at least one of said lower boundary and said upper boundary relative to said average of said extreme value, to generate at least one adapted boundary value, and using said at least one adapted boundary value to automatically initiate or end a next scan in said plurality of scans of the patient during said interventional procedure.

2. A method as claimed in claim 1 comprising generating an analog indicator signal, selected from the group consisting of optical signals, acoustic signals, and haptic signals, having a signal amplitude proportional to the detected pulmonary pressure when said pulmonary pressure falls below said lower boundary or exceeds said upper boundary.

3. A method as claimed in claim 2 comprising generating said indicator signal as an optical signal represented by a row of light-emitting diodes, comprising a central light-emitting diode that is located in a middle of said row, and representing a magnitude of said indicator signal by illumination of a corresponding number of said light-emitting diodes in said row, and causing said central light emitting diode to change emission color when said pulmonary pressure falls below said lower boundary or when said pulmonary pressure exceeds said upper boundary.

4. A method as claimed in claim 1 comprising, after each of said scans, automatically generating a calibration signal representing a desired value of said pulmonary pressure between a maximum value of said pulmonary pressure and a minimum value of said pulmonary pressure detected during each of said scans, and including said calibration signal in said computerized report file for each of said scans and, for a next scan during said interventional procedure, automatically adapting said at least one of said lower boundary said upper boundary relative to said calibration signal.

5. A method as claimed in claim 4 comprising generating an average of said calibration signals for said plurality of said scans and, for said next scan, automatically adapting said at least one of said lower boundary and said upper boundary relative to said average value of said calibration signal.

6. An image acquisition system for implementing a tomographically-assisted minimally-invasive interventional procedure of a patient, comprising:
   a tomographic data acquisition unit;
   a control unit configured to operate said tomographic data acquisition unit to implement a plurality of scans during said interventional procedure;
   a detector configured to, during a breath hold by a patient, measure a threshold value of a pulmonary pressure in the lungs of the patient in each of said scans;
   said detector also configured to continuously detect said pulmonary pressure, and supply the continuously detected pulmonary pressure to said control unit which is further configured to continuously detect successive inspiratory/expiratory positions of the patient therefrom;

said control unit being configured to conduct the plurality of scans during said interventional procedure and, for each of said scans in said plurality of scans, to automatically initiate acquisition of a tomographic slice image of the patient by said tomographic data acquisition unit, at an image acquisition time, when the continuously detected pulmonary pressure is within a tolerance range bounded by an upper boundary and a lower boundary of respectively different magnitudes around said threshold value of said pulmonary pressure, said tomographic slice image being comprised of image data;

said control unit being configured to automatically end said image acquisition when said pulmonary pressure assumes a value outside of said tolerance range, the initiating and ending of said image acquisition defining a scan;

said detector configured to continuously detect values of said pulmonary pressure including when said pulmonary pressure is below said lower boundary and when said pulmonary pressure is above said upper boundary, and said control unit being configured to identify a plurality of values representing an inspiratory/expiratory breathing volume of the patient from said plurality of values of said pulmonary pressure, and to generate a computerized report file of said scan that includes a representation of said breathing volume of the patient with respect to time; and said control unit being configured to identify an extreme value of said pulmonary pressure after each scan, selected from the group consisting of a maximum value and a minimum value, and including the identification of said extreme value in said computerized report file and, identifying an average value of the respective extreme values of said plurality of scans and, if said average of said extreme value is within said tolerance range, to automatically adapt at least one of said lower boundary and said upper boundary relative to said average of said extreme value, to generate at least one adapted boundary value, and to use said at least one adapted boundary value to automatically initiate or end a next scan in said plurality of scans of the patient by said tomographic data acquisition unit during said interventional procedure.

7. An image acquisition system as claimed in claim 6 wherein said measurement and display system is configured to generate an analog indicator signal, selected from the group consisting of optical signals, acoustic signals, and haptic signals, having a signal amplitude proportional to the detected pulmonary pressure when said pulmonary pressure falls below said lower boundary or exceeds said upper boundary.

8. An image acquisition system as claimed in claim 6 wherein said measurement and display system is configured to generate said indicator signal as an optical signal represented by a row of light-emitting diodes, comprising a central light-emitting diode that is located in a middle of said row, and to represent a magnitude of said indicator signal by illumination of a corresponding number of said light-emitting diodes in said row, and to cause said central light emitting diode to change emission color when said pulmonary pressure falls below said lower boundary or when said pulmonary pressure exceeds said upper boundary.

9. An image acquisition system as claimed in claim 6 wherein said measurement and display system is configured, after each of said scans, to automatically generate a calibration signal representing a desired value of said pulmonary pressure between a maximum value of said pulmonary pressure and a minimum value of said pulmonary pressure detected during each of said scans, and to include said calibration signal in said computerized report file for each of said scans and, for a next scan during said interventional procedure, to automatically adapt said at least one of said lower or said upper boundary relative to said calibration signal.

10. An image acquisition system as claimed in claim 9 wherein said control unit is configured to generate an average of said calibration signals for said plurality of said scans and, for said next scan, to automatically adapt said at least one of said lower boundary and said upper boundary relative to said average of said calibration signal.

11. A non-transitory computer-readable data storage medium encoded with programming instructions for operating an tomographic imaging system and a pulmonary pressure detector to implement a tomographically-assisted, minimally-invasive interventional procedure of a patient, said medium being loadable into a control arrangement for said tomographic imaging system and said detector, and said programming instructions causing said tomographic imaging system and said detector to:

during a breath hold of a patient in the tomographic imaging system, measure a threshold value of a pulmonary pressure in the lungs of the patient;

continuously detect successive inspiratory/expiratory positions of the patient by continuously detecting said pulmonary pressure;

conducting a plurality of tomographic scans of the patient during said interventional procedure and, for each of said scans in said plurality of scans, automatically initiate acquisition of a tomographic slice image of the patient, at an image acquisition time, when the continuously detected pulmonary pressure is within a tolerance range bounded by an upper boundary and a lower boundary of respectively different magnitudes around said threshold value of said pulmonary pressure, said tomographic slice image being comprised of image data;

automatically end said image acquisition in each of said scans when said pulmonary pressure assumes a value outside of said tolerance range, each of said scans being defined by the initiating and ending of said image acquisition;

continuously detect values of said pulmonary including when said pulmonary pressure is below said lower boundary and when said pulmonary pressure is above said upper boundary, and identify a plurality of values representing an inspiratory/expiratory breathing volume of the patient from said plurality of values of said pulmonary pressure, and generate a computerized report file of each of said scans that includes a representation of said breathing volume of the patient with respect to time; and after each of said scans, identify an extreme value of said pulmonary pressure, selected from the group consisting of a maximum value and a minimum value, and including the identification of said extreme value in said computerized report file and identifying an average value of the respective extreme values of said plurality of scans and, if said average of said extreme value is within said tolerance range, automatically adapt at least one of said lower boundary and said upper boundary relative to said average of said extreme value, to generate at least one adapted boundary value, and use said at least one adapted boundary value to automatically initiate or end a next scan in said plurality of scans of the patient during said interventional procedure.

* * * * *